United States Patent
Marsh et al.

[11] Patent Number: 6,152,925
[45] Date of Patent: Nov. 28, 2000

[54] METHOD AND APPARATUS FOR EXTERNAL FIXATION OF AN ELBOW

[75] Inventors: J. Lawrence Marsh, Iowa City, Iowa; Stephen B. Walulik, Phillipsburg, N.J.; Michael Bottlang; Curtis M. Steyers, both of Iowa City, Iowa

[73] Assignees: University of Iowa Research Foundation, Iowa City, Iowa; Electro-Biology, Inc., Parsippany, N.J.

[21] Appl. No.: 09/034,669

[22] Filed: Mar. 4, 1998

[51] Int. Cl.[7] ..................... A61B 17/56
[52] U.S. Cl. ................. 606/54; 606/55; 606/56
[58] Field of Search ............... 606/54, 53, 55, 606/56, 57, 58, 59, 60, 72, 73, 80, 96–97, 86; 523/20–24

[56] References Cited

U.S. PATENT DOCUMENTS

| | | | |
|---|---|---|---|
| 5,100,403 | 3/1992 | Hotchkiss et al. | 606/56 |
| 5,102,411 | 4/1992 | Hotchkiss et al. | 606/57 |
| 5,372,597 | 12/1994 | Hotchkiss et al. | 606/56 |
| 5,620,442 | 4/1997 | Bailey et al. | 606/54 |
| 5,662,650 | 9/1997 | Bailey et al. | 606/59 |

OTHER PUBLICATIONS

Hotchkiss, Robert N., M.D., Compass Elbow Hinge, undated, 20 pgs.
Pennig, PD Dr. D. and Gausepohl, Dr. T., The Elbow Fixator, undated, 23 pgs.

*Primary Examiner*—Michael Buiz
*Assistant Examiner*—Lien Ngo
*Attorney, Agent, or Firm*—Harness, Dickey & Pierce, P.L.C.

[57] ABSTRACT

An apparatus for adjustably securing the humerous, which is on a proximal side of elbow joint, relative to the ulna on the distal side of the elbow joint. The apparatus includes a central body having inner and outer ring members interconnected for relative rotation about a common mechanical axis adapted to align with the anatomical axis of the elbow joint. The central body defines a radiographic window for permitting lateral radiographic examination of the anatomical pivot axis of the elbow joint. The apparatus preferably includes a distraction mechanism for distracting the humerus perpendicular to the proximal end of the ulna.

20 Claims, 4 Drawing Sheets

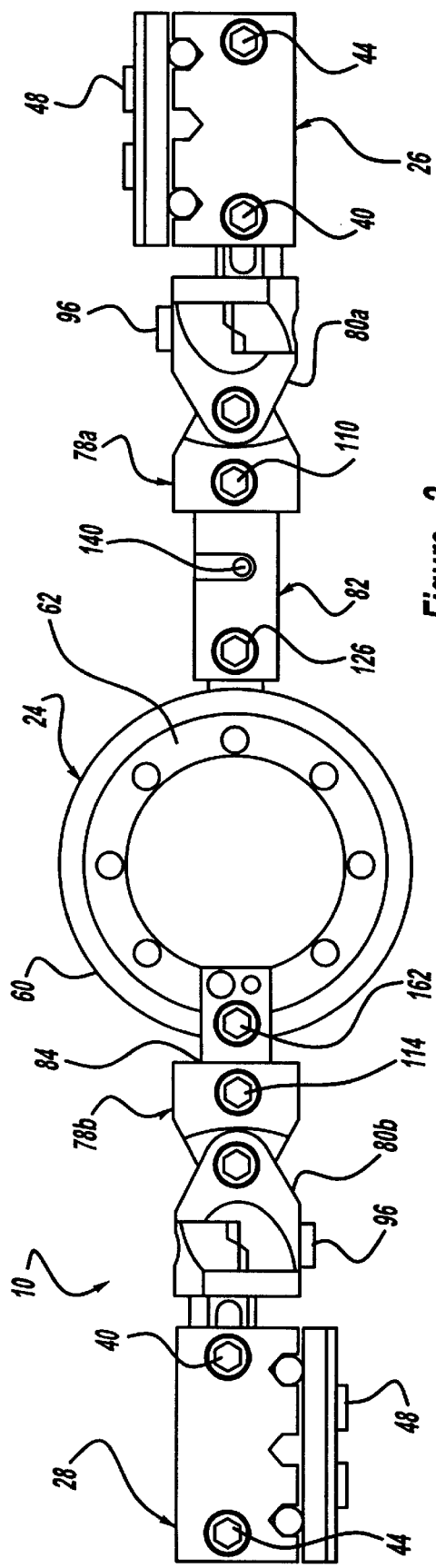
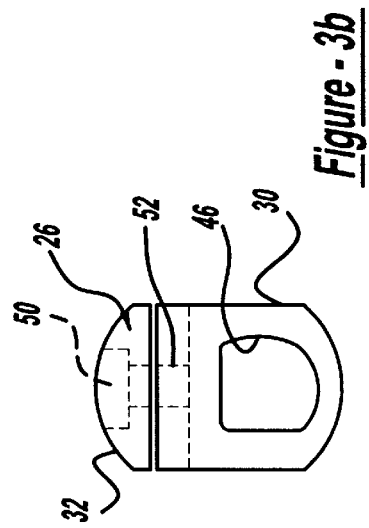
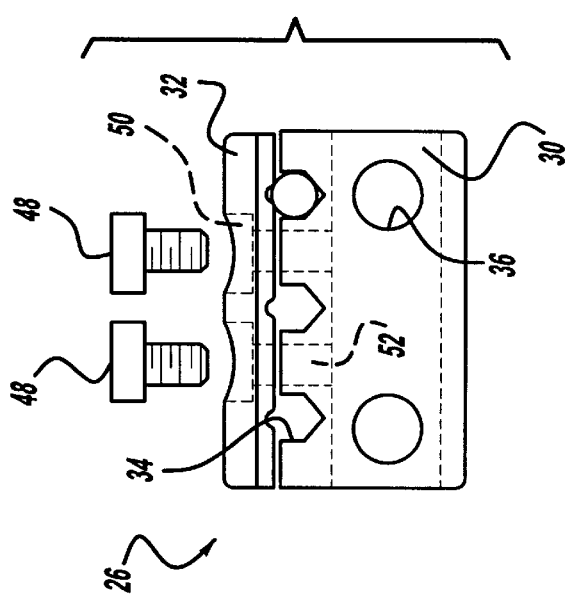

METHOD AND APPARATUS FOR EXTERNAL FIXATION OF AN ELBOW

BACKGROUND OF THE INVENTION

1. Field of the Invention

The present invention relates to an external fixator for use in orthopedic surgical applications, and more particularly to a method and apparatus for external fixation of an elbow.

2. Discussion of the Related Art

In various orthopedic surgical procedures, it is necessary to secure two bone portions in a relatively fixed relationship to each other. For example, the need for establishing such a secured relationship is often a result of a fracture which has occurred to the bone. To ensure that the bone can regenerate in the proper orientation and fuse the fracture, it is important that the bone portions be fixed and in the desired position during bone regeneration.

Various external fixation devices for the repair of traumatized bone are known. For example, U.S. Pat. No. 5,662,650 to Bailey et al. discloses an apparatus for the external fixation of large bones. The apparatus is illustrated to include a main body as well as a first and second bone screw clamps. The main body serves to allow the apparatus to axially rotate, thereby providing a proper longitudinal rotational location of the bone screws with respect to a bone. The first bone screw clamp is used to secure a first bone screw to the apparatus while permitting the first bone screw to be axially displaced from the main body. In a similar fashion, the second bone screw clamp functions to secure a second bone screw to the apparatus and to allow the second bone screw to be axially displaced with respect to the main body. U.S. Pat. No. 5,662,650 is incorporated by reference as if fully set forth herein.

In certain orthopedic surgical procedures, it is necessary to employ an external fixation device for immobilizing or restricting motion of a hinged joint such as the elbow joint. Many known devices for externally fixating an elbow joint require the insertion of an axis pin through the anatomical pivot axis. Another known device for elbow fixation is disclosed in U.S. Pat. No. 5,100,403 to Hotchkiss et al. which is entitled "Dynamic Elbow Support." The dynamic elbow support has proximal and distal support sections, means for rigidly connecting each support section to bone, and a pair of hinges connecting the support sections and pivoting at the joint. The pair of hinges permits movement of the support sections and their corresponding attached bone throughout flexion and extension. The hinge may be driven by a gear mechanism which may be disengaged by a clutch. The dynamic elbow support may also include a distraction mechanism for movement of the bones out of contact in the joint, while allowing for an active range of motion at the joint.

While known external fixators specifically designed for supporting an elbow joint may have proven to be acceptable for certain applications, such fixators are nevertheless susceptible to improvements that may enhance their performance.

SUMMARY OF THE PRESENT INVENTION

In general, the present invention relates to an external fixator for use as an orthopedic device for stabilizing a hinged joint. More specifically, the present invention relates to an external fixator which is operable to adjustably secure a skeletal element located on a proximal side of an elbow joint in a particular position with respect to a skeletal element on the distal side of the elbow joint. The external fixator includes a first means for receiving a bone screw which is preferably secured to the humerous. In addition, the external fixator includes a second means for receiving a second bone screw which is preferably secured to the ulna. The external fixator also includes a main body which is operable to connect the first means for receiving the first bone screw with a second means for receiving the second bone screw. The main body defines a radiographic window for permitting radiographic examination of the anatomical pivot axis of the elbow joint. The main body includes an inner ring member and outer ring member adapted to rotate relative to each other about a common center.

An advantage of the present invention is the provision of a method and apparatus for external elbow fixation which allows for optimal alignment through hinge positioning which is independent from bone pin placement.

A related advantage of the present invention is the provision of a method and apparatus for external fixation which affords flexible pin placement to avoid damage to local neurovascular structures and ligaments.

Another advantage of the present invention is the provision of a method and apparatus for external elbow fixation which permits movement of a hinge assembly relative to bone pins engaged with the humerus and ulna.

Another advantage of the present invention is the provision of a method and apparatus for external elbow fixation which allows complete radiographic access of the elbow joint from the lateral view to determine "best fit" hinge axis.

Another advantage of the present invention is the provision of a method and apparatus for external elbow fixation which facilitates elbow joint distraction.

Another advantage of the present invention is the provision of a method and apparatus for external fixation of an elbow joint eliminates the requirement for an elbow axis pin.

Another advantage of the present invention is the provision of a method and apparatus for external fixation of an elbow joint which distracts the humerous perpendicular to the tips of the olecranon and coronoid processes of the ulna.

Additional advantages and features of the present invention will become apparent from the following description and appended claims, taken in conjunction with the accompanying drawings.

BRIEF DESCRIPTION OF THE DRAWINGS

FIG. 2 is an enlarged view of the apparatus for external fixation of an elbow joint according to the teachings of the preferred embodiment of the present invention.

FIGS. 3A and B are illustrations showing the central body of the bone screw clamping assembly shown in FIG. 2 according to the teaching of the preferred embodiment of the present invention.

DETAILED DESCRIPTION OF THE PREFERRED EMBODIMENT

The following description of the preferred embodiment of the present invention is merely exemplary in nature and is in no way intended to limit the invention or its application or uses.

Figure 1A:
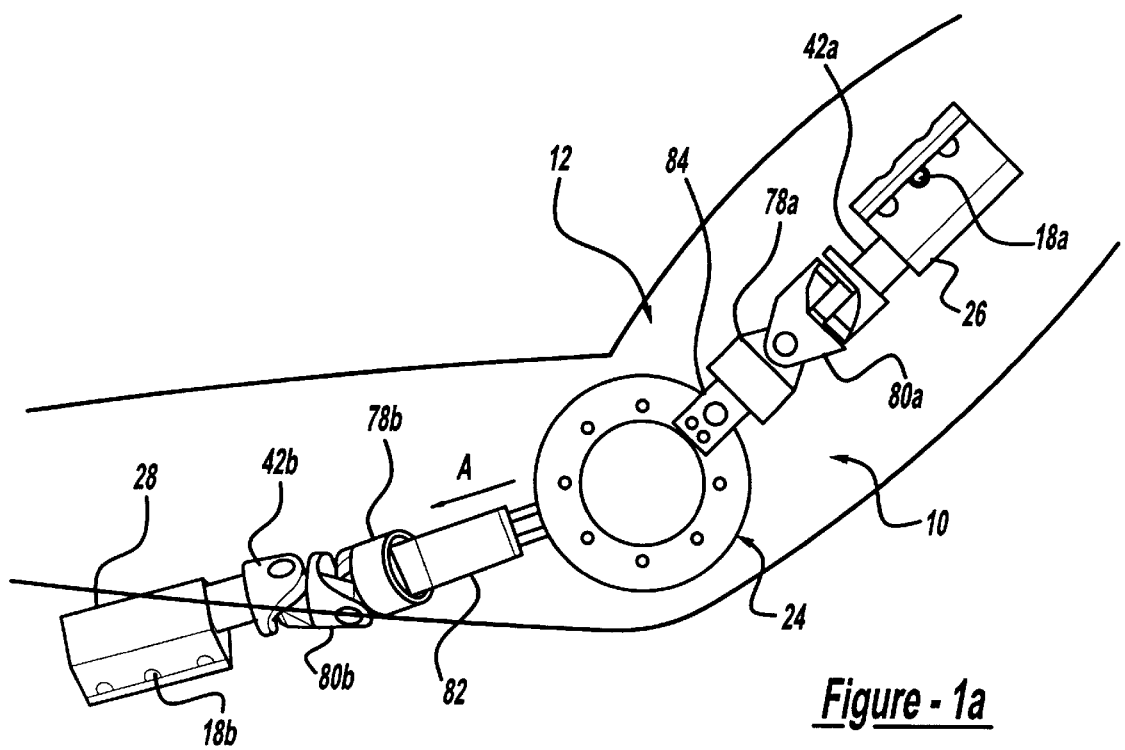
FIGS. 1A and 1B are views of the apparatus for external fixation of an elbow joint according to the teachings of the preferred embodiment of the present invention shown in operative association with a human elbow joint.
Figure 1B:
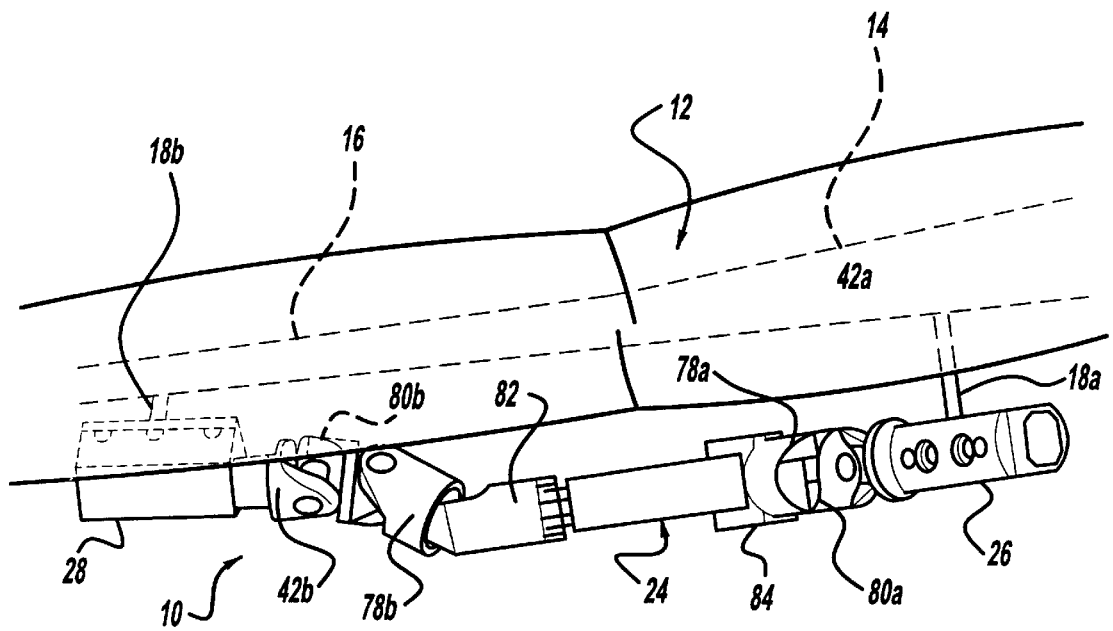
Figure 4A:
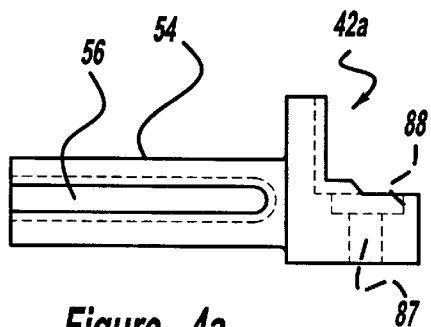
FIGS. 4A, 4B and 4C are illustrations of a rail member shown in FIG. 2 according to the teachings of the preferred embodiment of the present invention.
Figure 4B:
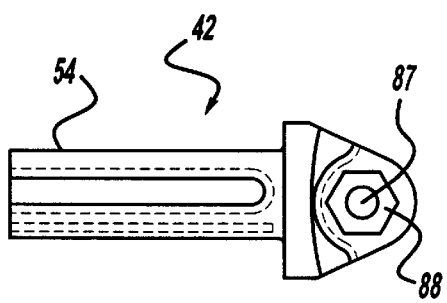
Figure 4C:
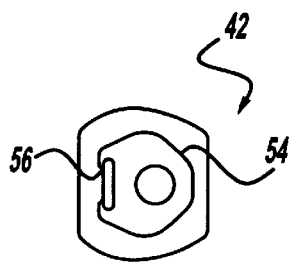
Figure 7A:
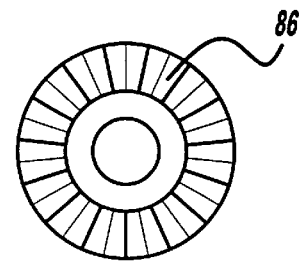
FIGS. 7A and 7B are illustrations showing one of the grooved locking washers shown in FIG. 2 according to the teachings of the preferred embodiment of the present invention.
Figure 5:
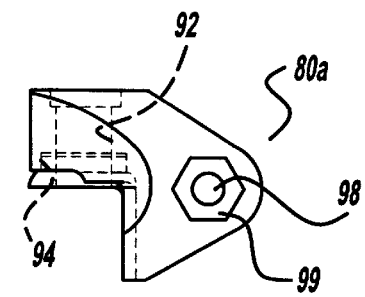
FIG. 5 is an illustration of a connector member shown in FIG. 2 according to the teachings of the preferred embodiment of the present invention.
Figure 7B:
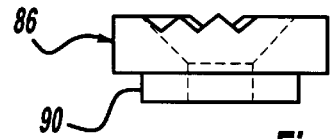
Figure 6A:
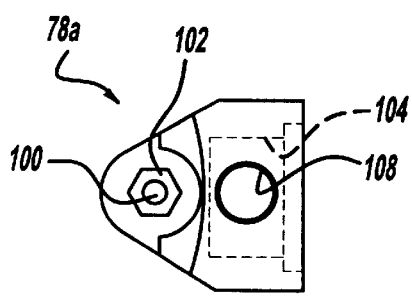
FIGS. 6A and 6B are illustrations of a rotational component shown in FIG. 2 according to the teachings of the preferred embodiment of the present invention.
Figure 6B:
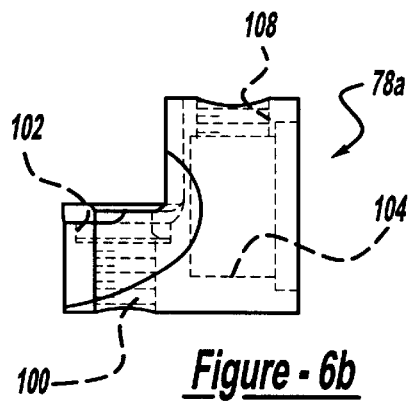

Referring to FIGS. 1A and 1B, an apparatus for external fixation of a hinged joint is generally identified with reference numeral 10. The apparatus 10 is illustrated operatively associated with a human elbow joint 12. However, it will become apparent to those skilled in the art that the teachings of the present invention have applicability to other hinged joints.

Before addressing the construction and function of the apparatus 10, a brief understanding of the pertinent elbow anatomy is warranted. The elbow joint 12 is a hinge type of synovial joint formed by the distal end of the humerus and the proximal ends of the radius and ulna. The elbow is a uniaxial joint and its movements consist of flexion and extension. The trochlea and capitulum of the humerus articulate with the trochlear notch of the ulna and the head of the radius, respectively.

FIG. 1B shows in a simplified manner, the apparatus 10 interconnected to a first bone 14 on the proximal side of the elbow joint 12 and a second bone 18b on the distal side of the joint. In the exemplary arrangement illustrated, the first bone is the humerus 14 and the second bone is the ulna 16.

With continued reference to FIGS. 1A and 1B, the apparatus 10 is shown preferably connected to the humerus 14 through at least a first bone screw 18a and to the ulna 16 through at least a second bone screw 18b. By securing the humerus 14 and ulna 16 in this manner, the anatomical pivot axis of the elbow joint 12, which is located therebetween, may be stabilized. Again, while the apparatus 10 is specifically shown associated with an elbow joint 12, it is to be understood that the teachings of the present invention may be adapted for use with other hinged joints of the body.

With continued reference to FIGS. 1A and 1B and additional reference to FIGS. 2–10, the apparatus 10 is shown to generally comprise a central ring assembly 24, a first bone screw clamping assembly 26 and a second bone screw clamping assembly 28. The ring assembly or main body 24 is adjustably interconnected to both of the first and second bone screw clamping assemblies 26 and 28 to allow for adjustment of the bone screws 18 relative to the mechanical pivot axis. The first bone screw clamping assembly 26 is used to secure the first bone screw 18a to the apparatus 10 while permitting the first bone screw 18a to be axially displaced from the central ring assembly 24. The second bone screw clamping assembly 28 similarly is used to secure the second bone screw 18b to the apparatus 10 while permitting the second bone screw 18b to be axially displaced from the central ring assembly 24.

The principal focus of the present invention relates to the construction and operation of the central ring assembly 24 and the adjustable interconnections between the central ring assembly 24 and the first and second clamping assembly 26 and 28. In this regard, it will be understood that the first and second bone screw clamping assemblies 26 and 28 may be of any suitable configuration for receiving the bone screws 18. For purposes of fully describing the exemplary embodiment illustrated throughout the drawings, the first and second clamping assembly 26 and 28, as well as the central ring assembly 24 and the interconnections between the central ring assembly 24 and the first and second bone screw clamping assembly 26 and 28, will be more fully discussed below.

The first bone screw clamping assembly 26 will be described in greater detail with reference to FIGS. 3A–3B. It is to be understood that while only the first bone screw clamp 26 is being described, the second bone screw clamp 28 will have a similar construction. The first bone screw clamping assembly 26 includes a base portion 30 and a cover portion 32. The base portion 30 preferably serves to receive two bone screws 18a in two of a plurality of grooves 34, while the cover portion 32 serves to secure the bone screws 18a within the grooves 34. The grooves 34 include two contact surfaces which are substantially planar so as to permit line contact of the bone screws 18 in two positions within the grooves 34. Since the first bone screw 18a also engages the cover portion 32 of the first bone screw clamping assembly 26, the bone screws 18 engage the first bone screw clamping assembly 26 in three positions (i.e., along the contact surfaces as well as on the cover portion 32). This provides line contact for the bone screw 18 which secures the bone screws 18 in a more effective manner than if the grooves 34 were cylindrical.

The base portion 32 of the bone screw clamping assembly 26 further includes a first aperture 36 and a second aperture 38. The first aperture 36 is used to receive a threaded member 40 which serves to secure a rail member 42 in a locked position as will be more fully discussed below. The second aperture 38 is used to receive a threaded member 44 which is able to secure a compression/distraction member (not shown) within a D-shaped central bore 46 of the bone screw clamping assembly 26. One suitable compression/distraction member is shown and described in U.S. Pat. No. 5,662,650.

The cover portion 32 of the first bone screw clamping 26 is secured to the base portion 30 by means of two screws 48. To accommodate these screws 48, the cover portion 32 of the bone screw clamping assembly 26 includes two apertures 50 (shown in phantom in FIGS. 3(A) and 3(B)) which mate with corresponding apertures 52 in the base portion 30 of the bone screw clamp 26. Accordingly, upon secured threaded engagement of the screws 48 within the apertures 50 and 52, the cover portion 32 of the bone screw clamp 26 may be secured to the base portion 30 of the bone screw clamp 26.

To provide means for laterally displacing the first bone screw clamp 26 with respect to the central body 24, the bone screw clamping assembly 26 further includes the rail member 42. The rail member 42, which is illustrated most clearly in FIGS. 4A–4C, includes a D-shaped extension 54 which is able to receive in the D-shaped bore 46 of the bone screw clamping assembly 26. Because of the cross-sectional shape of the D-shaped extension 54, the base portion 30 of the bone screw clamping assembly 26 is able to slide on the D-shaped extension 54 of the rail member 42, though the base portion 30 is unable to rotate with respect to the D-shaped extension 54.

The rail member 42 further includes a groove 56 which is disposed on the surface of the D-shaped extension 54. The location of the groove 56 is such as to permit the groove 56 to be located adjacent to the aperture 36 when the D-shaped extension 54 of the rail member 42 is inserted into the D-shaped bore 46 of the base portion 30. As will be apparent to those skilled in the art, the threaded member 40 can then be inserted into the aperture 36 of the base portion 30 of the bone screw clamping assembly 26 so as to securely engage the groove 56 of the D-shaped extension 54 thereby preventing axial movement of the base portion 30 with respect to the rail member 42. In the preferred embodiment, the groove 56 includes graduated markings (not specifically shown) indicating the relative amount of longitudinal displacement of the bone screw clamping assembly 26 relative to the central body 24.

To provide means for displacing the second bone screw clamp 28 with respect to the central body 24, the second bone screw clamp 28 similarly includes a second rail member 42b. As with the first rail member 42a, the second rail member 42b has a D-shaped extension 54 which is able to receive the D-shaped bore 46 of the second bone screw clamp 28. Again, because of the cross-sectional shape of the D-shaped extension 54, the base portion 30 of the second bone screw clamp 28 is able to slide on the D-shaped extension 54 of the second rail member 42b, though the base portion 30 is unable to rotate with respect to the D-shaped extension 54.

Figure 10:
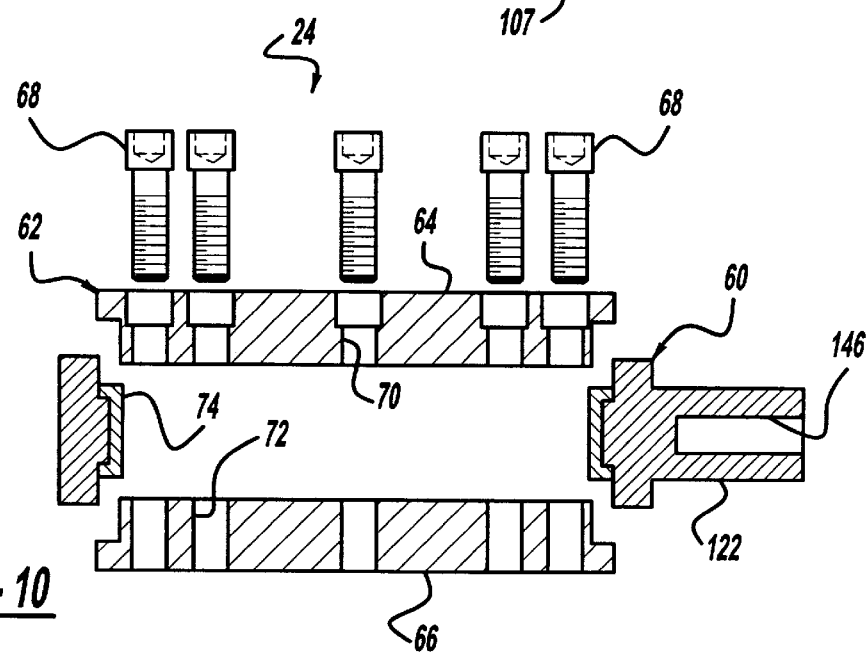
FIG. 10 is an exploded view of the ring assembly shown in FIG. 2 according to the teachings of the preferred embodiment of the present invention, illustrated in cross section.

With specific reference to FIGS. 2 and 10, the central ring assembly 24 will now be described in greater detail. The ring assembly 24 is shown to generally include an outer ring member 60 and an inner ring member 62. The outer and inner ring members 60 and 62 are coincentrially arranged and adapted to rotate relative to each other about a common centerpoint. In the embodiment illustrated, the inner ring member 62 includes first and second halves 64 and 66. The first and second halves 64 and 66 are joined by a plurality of threaded fasteners 68. To accommodate these fasteners 68, the first half 64 includes apertures 70 which mate with corresponding apertures 72 in the second half 66. Upon secured threaded engagement of the threaded fastener 68 with the aperture 72 in the second half 66, the first and second halves 64 and 66 are interconnected and the outer ring member 60 is rotatably captured therebetween. In the embodiment illustrated, a suitable bearing 74 is provided between adjacent surfaces of the inner and outer members 60 and 62.

To provide means for adjustably interconnecting the central ring assembly 24 with the first clamping assembly 26, the apparatus 10 of the present invention is shown to include a first rotational component 78a, a first connection member 80a, and an outer ring attachment component 82. To provide means for adjustably interconnecting the central ring assembly 24 with the second clamping assembly 28, the apparatus 10 is shown to generally include a second rotational component 78b, a second connection member 80b and an inner ring attachment component 84. It is to be understood that while only the first rotational component 78a and the first connection member 80a are being described, the second rotational component 78b and the second connection member 80b, respectively, have a similar construction.

A pair of grooved locking washers 86 is disposed between the first rail member 42a and the first connection member 80a, as well as between the second rail member 42b and the second connection member 80b. In particular, the first rail member 42a has an aperture 87 with a hex-shaped recess 88 for receiving a base portion 90 of the washer 86, while the second rail member 42b also has an aperture with a hex-shaped recess for receiving the base portion 90 of the washer 86.

In a similar fashion, the first connection member 80a also includes an aperture 92 with a hex-shaped recess 94 for receiving the base portion 90 of the washer 86, while the second connection member 80b also has an aperture with a hex-shaped recess for engaging the base portion 90 of the washer 86. Because the groove surfaces of adjacent washer 86 engage each other, the first rail member 42a is secured to the first connection member 80a upon secured threaded engagement of a screw 96, while the second rail member 42b is secured to the second connection member 80b upon threaded engagement of the screw 96. The first and second connection members 80a and 80b permit approximately 60° of relative rotation between the first and second bone screw clamps 26 and 28, respectively, with respect to the central body 24.

The first and second connection members 80a and 80b are also secured to the first rotational component and second rotational component 78a and 78b, respectively, each by a pair of locking washers 86. In this regard, first connection member 80a includes an aperture with a hex-shaped recess for receiving the base portion 90 of the washer 86, while the second connection member 80b similarly has an aperture with a hex-shaped recess for receiving the base portion 90 of the washer 86. In a similar fashion, the first rotational component 78a also has an aperture 100 with a hex-shaped recess 102 for receiving the base portion 90 of the washer 86, while the second rotational component also has an aperture with a hex-shaped recess for receiving the base portion 90 of the washer 86. The grooves in the washers 86 allow more secure attachment between the first and second connection members 80a and 80b and the first and second rotational components 78a and 78b, respectively, when they are secured by the bolts 96.

The first rotational component 78a defines a bore 104 which is able to receive a male extension portion 106 of the outer ring connection member 82 and includes an aperture 108 which is able to receive a threaded member 110 (shown in FIG. 2). The male extension 106 includes a reduced diameter portion 107 which is able to be located proximate to the aperture 108 in the first rotational component 78a. When the threaded member 110 is inserted through the aperture 108 in the first rotational component 78a and is allowed to engage the male extension portion 106 of the outer ring connection member 82, the first rotational component 78a and the outer ring connection member 82 are securely locked so as to prohibit relative rotational movement.

Similarly, the second rotational component 78b defines a bore which is able to receive a male extension portion 112 of the inner ring connection member 84 and includes an aperture which is able to receive a threaded member 114. The male extension portion 112 includes a reduced diameter portion 116 which is able to be located proximately to the aperture in the second rotational component 78b. When the threaded member 114 is inserted through the aperture in the second rotational component 78b and is allowed to engage the male extension portion 112, thereby relative rotation therebetween is prevent.

Figure 9:
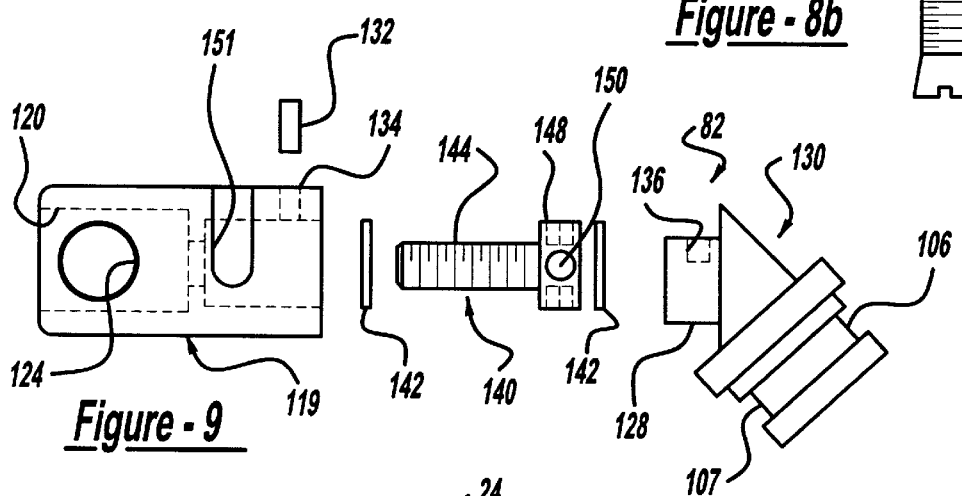
FIG. 9 is an exploded view of an outer ring attachment component shown in FIG. 2 according to the teachings of the preferred embodiment of the present invention.

The outer ring attachment component 84 is shown most clearly in FIG. 9 to include a connector member 119 which defines an internal bore 120. A first end of the bore 120 is adapted to receive a male extension 122 integrally formed with the outer ring member 60. The connector member 119 further includes a threaded aperture 124 which intersects the bore 120 and is adapted to receive a threaded fastener 126. The threaded fastener 126 operates when tightened to interconnect the outer ring member 60 and the outer ring attachment component 82 and prevent relative movement therebetween.

A second end of the bore 120 is adapted to receive a male extension 128 carried by an angled member 130 which also carries the male extension portion 106. The angled member 130 is securely attached to the connector member 119 through a pin 132 which is adapted to pass through an aperture 134 which intersects the bore 120 and engages a corresponding aperture 136 provided in the male extension 128. In the embodiment illustrated, the angle between the male extension 128 and the male extension portion 106 of the angled member 130 is approximately 45°.

To provide means for translating the outer ring attachment component 82 relative to the ring assembly 24, the outer ring attachment component 82 includes a threaded member 140 disposed within the bore 120. The threaded member 140 is rotatably supported by a pair of suitable bearings 142 and includes an externally threaded shaft 144 adapted to engage an internally threaded bore 146 provided in the male extension portion 122 of the outer ring member 60. The threaded fastener 140 further includes a head 148 formed to include a plurality of apertures 150. The apertures 150 are accessible through an elongated slot 151 provided in the connector member 119. In use, translation of the connector member 119 is accomplished by rotating the threaded fastener 140 with an alien wrench or similar tool adapted to engage one of the apertures 150 provided in the head 148. The angled member 130 allows the apparatus 10 to distract the humerous perpendicular to the proximal end of the ulna (i.e., perpendicular to the tips of the olecranon and coronoid processes of the ulna). The direction of distraction is identified in FIG. 1A by arrow A.

Figure 8A:
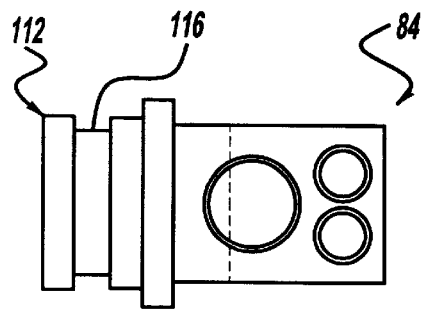
FIGS. 8A and 8B are illustrations of an inner ring attachment component shown in FIG. 2 according to the teachings of the preferred embodiment of the present invention.
Figure 8B:
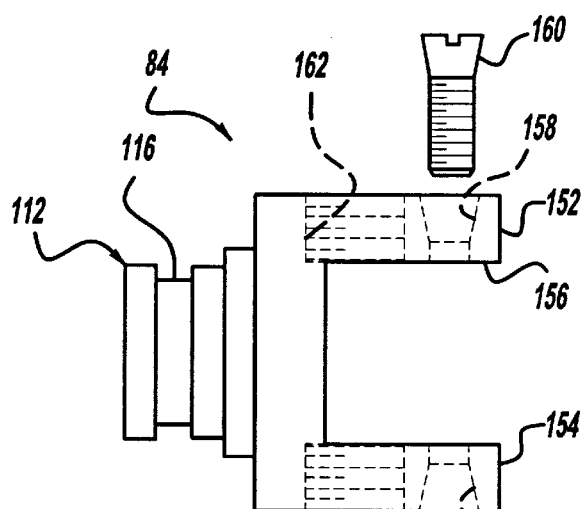

Turning to FIGS. 8A and 8B, the inner ring attachment component 84 is shown to include first and second spaced apart flanges 152 and 154 which define a recess 156 therebetween adapted to rotatably accommodate the ring assembly 24. Both of the flanges 152 and 154 include a pair of apertures 158 adapted to receive a threaded fastener 160. The threaded fastener 160 is adapted to pass through the aperture and lockingly engage corresponding apertures (not specifically shown) provided in the inner ring member 62 of the ring assembly 24. The inner ring connection component 84 allows the second bone clamping assembly 28 to be interconnected to the inner ring member 62 while allowing the inner ring member 62 to rotate relative to the outer ring member 60. In this manner, the humerous 14 and ulna 16 are permitted to rotate relative to one another about the anatomical pivot axis of the elbow 12.

The first flange 152 includes a second threaded aperture 162. The second threaded aperture 162 is adapted to receive a threaded fastener 164 (shown in FIG. 2). Upon tightening, the threaded fastener 164 is adapted to engage the outer ring member 60 and selectively prevent relative rotation of the inner and outer ring members 60 and 62.

The foregoing discussion discloses and describes merely exemplary embodiments of the present invention. One skilled in the art will recognize from such discussion and from the accompanying drawings and claims, that various changes, modifications and variations can be made therein without departing from the spirit and scope of the invention.

What is claimed is:

1. An apparatus for external fixation of a joint having an anatomical pivot axis interdisposed between first and second skeletal elements, the apparatus comprising:

a first bone screw adapted to be connected to the first skeletal element;

a second bone screw adapted to be connected to the second skeletal element;

a central body including inner and outer ring members interconnected for relative rotation about a common mechanical pivot axis, said outer ring member including first and second torroidal shaped halves, said inner ring member rotatable captured between said first and second halves;

first bone screw clamp receiving said first bone screw, said first bone screw clamp interconnected to said central body; and a second bone screw clamp receiving said second bone screw, said second bone screw clamp interconnected to said central body.

2. The apparatus for external fixation of a joint of claim 1, wherein said central body defines a closed circle having an open center.

3. The apparatus for external fixation of a joint of claim 1, further comprising a distraction mechanism for distracting said second bone screw relative to the anatomical pivot axis.

4. The apparatus for external fixation of a joint of claim 3, wherein the distraction mechanism includes a rotatable element radially extending from the central body.

5. The apparatus for external fixation of a joint of claim 1, further comprising an outer ring connection member for interconnecting said outer ring with said second bone screw, said outer ring connection member radially extends from said outer ring member and including said distraction mechanism.

6. The apparatus for external fixation of a joint of claim 5, wherein said outer ring connection member includes a first end having a longitudinal axis parallel to a plane including said outer ring member and a second end having a longitudinal axis oriented at an oblique angle relative to said longitudinal axis of said first end.

7. The apparatus for external fixation of a joint of claim 1, further comprising an inner ring connection member including first and second spaced apart flanges defining a recess therebetween, said recess receiving said ring assembly such that said outer ring member may rotate relative to said inner ring connection member.

8. The apparatus for external fixation of a joint of claim 1, wherein the apparatus is for external fixation of an elbow joint.

9. An apparatus for external fixation of a joint having an anatomical pivot axis interdisposed between first and second skeletal elements, respectively, the apparatus comprising:

a first bone screw adapted to be connected to the first skeletal element;

a second bone screw adapted to be connected to the second skeletal element;

a central body including inner and outer ring members interconnected for relative rotation about a common mechanical pivot axis, said central body defining a closed circle having an open center;

first bone screw clamp receiving said first bone screw, said first bone screw clamp interconnected to said central body; and a second bone screw clamp receiving said second bone screw, said second bone screw clamp interconnected to said central body.

10. The apparatus for external fixation of a joint of claim 9, further comprising a distraction mechanism for distracting said second bone screw relative to the anatomical pivot axis.

11. The apparatus for external fixation of a joint of claim 10, wherein the distraction mechanism has a rotatable element radially extending from the central body.

12. The apparatus for external fixation of a joint of claim 10, further comprising an outer ring connection member for interconnecting said outer ring with said second bone screw, said outer ring connection member radially extends from said outer ring member and including the distraction mechanism.

13. The apparatus for external fixation of a joint of claim 12, wherein said outer ring connection member includes a first end having a longitudinal axis parallel to a plane including said outer ring member and a second end having a longitudinal axis oriented at an oblique angle relative to said longitudinal axis of said first end.

14. The apparatus for external fixation of a joint of claim 9, further comprising an inner ring connection member including first and second spaced apart flanges defining a recess therebetween, said recess receiving said ring assembly such that said outer ring member may rotate relative to said inner ring connection member.

15. The apparatus for external fixation of a joint of claim 1, wherein the apparatus is for external fixation of an elbow joint.

16. An apparatus for external fixation of a joint having an anatomical pivot axis interdisposed between first and second skeletal elements, respectively, the apparatus comprising:

a first bone screw adapted to be connected to the first skeletal element;

a second bone screw adapted to be connected to the second skeletal element;

a central body including inner and outer ring members interconnected for relative rotation about a common mechanical pivot axis;

first bone screw clamp receiving said first bone screw, said first bone screw clamp interconnected to said central body;

a second bone screw clamp receiving said second bone screw, said second bone screw clamp interconnected to said central body; and a distraction mechanism for distracting said second bone screw relative to the anatomical pivot axis, said distraction mechanism having a rotatable element radially extending from said outer ring member.

17. An apparatus for external fixation of a joint of claim 16, further comprising an outer ring connection member for interconnecting said outer ring with said second bone screw, said outer ring connection member radially extends from said outer ring member and including said distraction mechanism.

18. An apparatus for external fixation of a joint of claim 17, wherein said outer ring connection member includes a first end having a longitudinal axis parallel to a plane including said outer ring member and a second end having a longitudinal axis oriented at an oblique angle relative to said longitudinal axis of said first end.

19. An apparatus for external fixation of a joint of claim 16, further comprising an inner ring connection member including first and second spaced apart flanges defining a recess therebetween, said recess receiving said ring assembly such that said outer ring member may rotate relative to said inner ring connection member.

20. An apparatus for external fixation of a joint of claim 16, wherein the apparatus is for external fixation of an elbow joint.

* * * * *